United States Patent [19]

Brooks

[11] 4,375,961
[45] Mar. 8, 1983

[54] SONIC BONDING MEANS FOR ORTHODONTICS

[76] Inventor: Phillip A. Brooks, 436 NW. 46 Ter., Oklahoma City, Okla. 73118

[21] Appl. No.: 306,414

[22] Filed: Sep. 28, 1981

[51] Int. Cl.³ .............................................. A61C 3/00
[52] U.S. Cl. ....................................... 433/4; 433/159; 156/580.1; 228/1 R
[58] Field of Search .................. 433/3, 4, 9, 119, 159; 156/73.1, 580.1, 580.2; 228/1 B, 1 R, 1 A, 110

[56] References Cited

U.S. PATENT DOCUMENTS

| | | | |
|---|---|---|---|
| 3,053,124 | 11/1962 | Balamuth et al. | 228/1 |
| 3,477,119 | 11/1969 | Smith | 156/580.1 |
| 3,480,492 | 11/1969 | Hauser | 156/73.1 |
| 3,529,660 | 9/1970 | Obeda | 228/1 |
| 3,580,460 | 5/1971 | Lipschutz | 228/1 B |
| 3,602,421 | 8/1971 | Spratt | 433/119 |
| 3,657,056 | 4/1972 | Winston et al. | 156/580.2 |
| 3,727,619 | 4/1973 | Kuris | 156/73.1 |
| 4,035,919 | 7/1977 | Cusato | 433/3 |
| 4,155,164 | 5/1979 | White | 433/3 |
| 4,321,288 | 3/1982 | Ostreicher | 427/224 |

FOREIGN PATENT DOCUMENTS 2316911  2/1977  France ................ 433/159

*Primary Examiner*—Gene Mancene
*Assistant Examiner*—John J. Wilson
*Attorney, Agent, or Firm*—Head, Johnson & Stevenson

[57] ABSTRACT

A sonic apparatus for bonding an orthodontic bracket to a tooth, comprising a pincer-type element having arms for holding the bracket and an attached sonic transmission line for applying a sonic frequency to the bracket through the arms of the pincer element.

4 Claims, 19 Drawing Figures

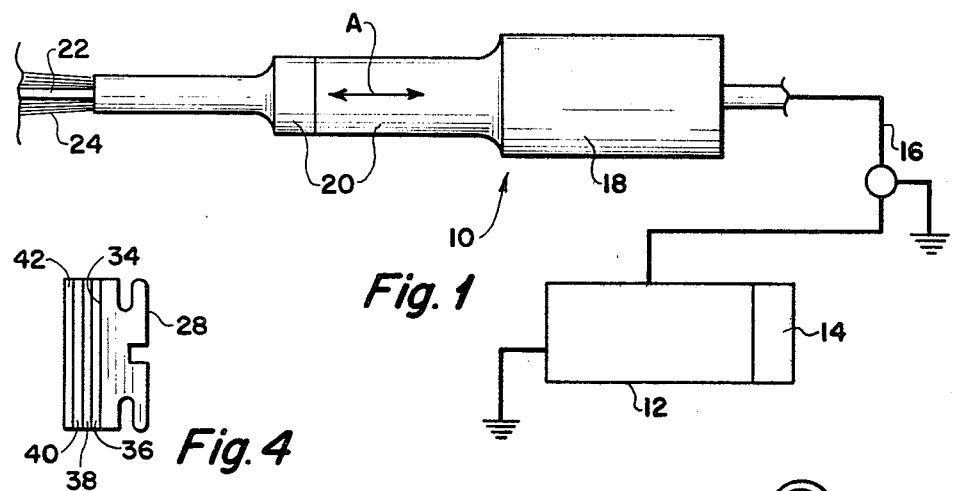
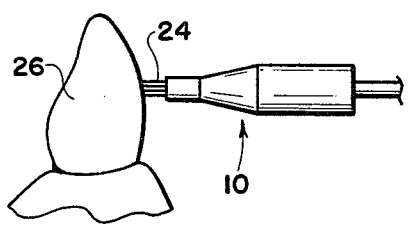
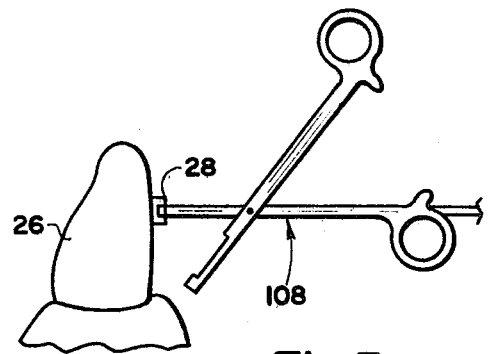
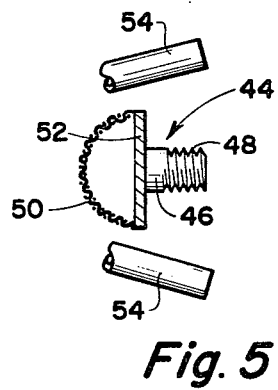
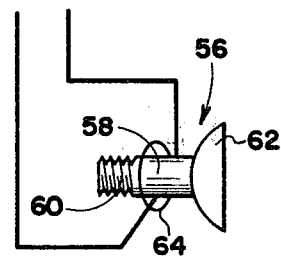

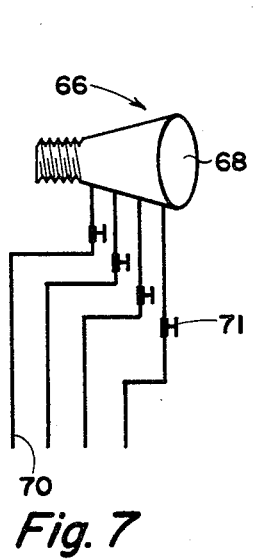
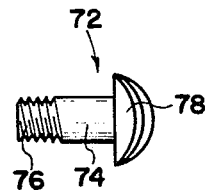
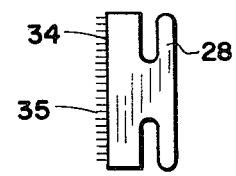
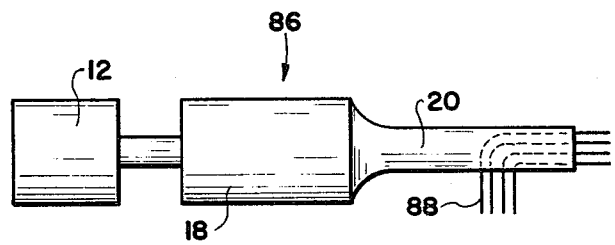
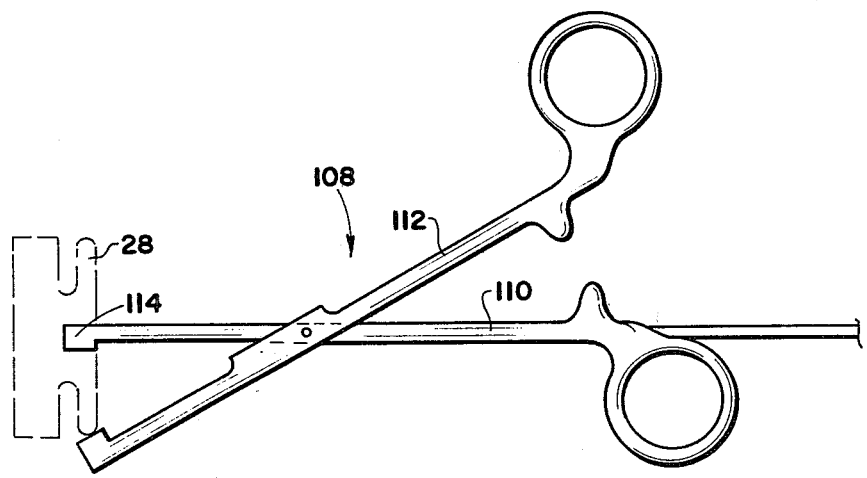
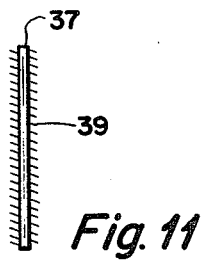

SONIC BONDING MEANS FOR ORTHODONTICS

CROSS-REFERENCE TO RELATED APPLICATIONS

This application is related to my co-pending applications Ser. No. 232,425, filed Feb. 5, 1981, and entitled "Sonic Brush", and Ser. No. 194,869, filed Oct. 7, 1980, and entitled "Sonic Integument Removal Device and Method."

BACKGROUND OF THE INVENTION

1. Field of the Invention

This invention relates to improvements in method and means for bonding of one article to another and more particularly, but not by way of limitation, to a sonic method and means for bonding said articles together.

2. Description of the Prior Art

The importance and usefulness of sonics and ultrasonics are becoming more and more apparent, and there is presently considerable activity in industry for expanding the utilization of these energies. There are many areas wherein the use of sonics and ultrasonics may be utilized for reducing time required for completing or accomplishing many work operations, with the end result being also improved. In the dental art, for example, there has been activity in expanding the use of sonics as shown in the Mumaw U.S. Pat. No. 3,332,149, issued July 25, 1967, and entitled "instrument for Loosening Teeth With High-Frequency Vibrations." The Mumaw Patent discloses an instrument having transducers disposed within a housing and operably connected between an ultrasonic generator and horns for transmitting reciprocal motion to the horns. The horns are secured to the diametrically opposed sides of a driving head which is oscillated as the horns reciprocate in alternating and opposite directions. The driving head is provided with tooth engaging means, and the high-frequency oscillation of the driving head is transmitted to the tooth for gently loosening the tooth in its alveolar socket. In the case of an orthodontic application, the tooth is loosened only sufficiently for altering the position thereof in the surrounding tissue, whereas in a tooth extraction operation, or the like, the tooth is loosened completely for a quick and efficient removal of the tooth with a minimum of damage to the surrounding portions of the alveolar bone. Other sonic applications have been set forth in the dental art, such as that shown in the Rapuano U.S. Pat. No. 3,995,372, issued Dec. 7, 1976, and entitled "Method and Apparatus for Securing a Retention Pin to a Tooth", the Takemoto et al U.S. Pat. No. 4,127,125, issued Nov. 28, 1978, and entitled "Devices for Transmitting Ultrasonic Waves to Teeth", and the Bailey U.S. Pat. No. 3,728,562, issued Dec. 27, 1955, and entitled "Vibrating Device for Denture Material".

The high-frequency method for facilitating the straightening of teeth shown in the aforementioned Mumaw patent has certain disadvantages in that the movement of the loosened teeth during an orthodontic procedure following the Mumaw method is usually too great, or not of sufficient "finesse" and the teeth may revert to the original position thereof too readily. As a result, the time honored method of straightening of the teeth through the use of orthodontic brackets bonded to the teeth, and associated elements and procedures is still in widespread use today, and it is common practice in a tooth straightening procedure to clean each tooth carefully prior to an etching of the tooth for preparing thereof to receive the orthodontic bracket, or the like. The efficient cleaning of the tooth or teeth is time consuming and exacting, as is the etching operation, and in addition, it is extremely important to maintain the cleaned and etched tooth or teeth completely dry prior to the attachment of the bracket to the tooth. This is because moisture is a detriment to the bonding process required for attaching the bracket to the tooth, and since the normal bracket is usually quite small in configuration, presenting a very small area for bonding of the bracket to the tooth, the efficiency of the bonding is exceedingly important. Of course, other dental procedures are time consuming and costly, such as the making of tooth or teeth impressions, molding of dentures, and the like, self-cleaning sterilization, mixing of amalgum, and the like, and other such procedures which may be improved through the use of sonics or ultrasonics. Of course, it has also been found that many of the problems encountered in the care and control of teeth are generally similar to some of the problems encountered in connection with the care and repair of bone structures of the body.

To further emphasize the processes involved in the bonding of orthodontic brackets to teeth, the usual steps comprise an initial cleaning of the tooth, or teeth, followed by an etching process accomplished by the application of phosphoric acid, or the like, to the surface of the tooth and for an extended period of time. The acid or acids used for the etching of the teeth normally penetrate the teeth, dissolving enamel prisms or a honeycomb of approximately thirty microns deep. These prismatic rods usually average four microns in diameter. Subsequent to the etching of the tooth, the tooth is again cleaned, and the etched and cleaned tooth is maintained substantially absolutely dry in preparation for the bonding of the bracket member thereto. It will be apparent that the requirement for keeping the tooth dry is difficult to achieve in view of the quantity of saliva normally present in the mouth surrounding the tooth and any reduction of the time required for the bonding of the bracket to the tooth is a great advantage, not only for the foregoing reasons, but also in that a saving of time in the bonding operation considerably alleviates the maintaining of the tooth in the required dry condition.

SUMMARY OF THE INVENTION

The present invention is generally concerned with the application of sonics and/or ultrasonics in dentistry, and particularly in facilitating the bonding of brackets to teeth, or the like. The ultrasonic fiber transmitting brush shown in my aforementioned application Ser. No. 232,425 and the general concept thereof is especially useful in the dental field for the cleaning and etching of the teeth prior to the bonding of a bracket thereto, as well as improving the bonding operation itself. A tooth cleaning operation may be accomplished very quickly with the use of my sonic brush means, and another adaptation of the sonic brush may be utilized for an efficient and rapid etching of the tooth subsequent to the cleaning thereof. The secondary cleaning step may also be effectively achieved with my sonic brush concept, thus quickly and efficiently preparing the tooth for receiving an orthodontic bracket. The fibers or bristles of the sonic brush may be particularly arranged to provide a "prism" contacting area for engagement with the tooth during the etching operation for matching of the structure of the tooth enamel.

In the bonding of the bracket to the tooth, or the like, it has been found that any suitable bonding agent in combination with the application of sonic or ultrasonic frequency to the bracket provides a rapid and extremely efficient bonding action. Some bonding materials are very reactive to the application of ultrasonics and provide a quick and stronger bond than is attained under the usual bonding process. One such substance that does not require mixing, such as required in the use of many other dental materials, is superglue, a fast-acting cyanoacrylate. Some brands have been found to produce more superior results than others, with Krazy Glue (a trademark of Krazy Glue, Inc.) being exceptionally efficient. A dental mix material for bonding purposes that has also been found to be efficient is manufactured by Lee Pharmaceuticals, a firm located in California. The product is sold under the name Lee Unique or Lee Instabond, and requires a two stage application process of a primer and adhesive. When using the Lee Pharmaceuticals products for bonding the orthodontic bracket to a tooth, the primer coating is normally applied to the tooth surface and on the bracket and subsequently the adhesive is applied prior to the bonding process. Of course, there are many other readily available bonding products applicable for use with my bonding method and means. In fact, in some instances, it has been found that applying a plurality of superimposed layers of cooperating materials directly to the orthodontic bracket, either in an encapsulated or layered form, or not, as desired, prior to impressing or applying ultrasonic frequencies on the bracket produces an exceptionally strong and rapid bonding of the bracket to the tooth. In addition, it has been found that my method and means is also efficient in the mending or repairing of damaged bones, such as by a bonding operation with the use of bone powder, or the like.

Of course, it will be apparent that it is also necessary to ultimately remove the bracket from the bonded engagement with the tooth, and the cleaning implement shown in my aforementioned pending application Ser. No. 194,869 can be readily modified for attachment to the bracket for impressing ultrasonic frequencies on the bonded bracket whereupon the connection between the bracket and the tooth may be readily released for a quick and easy removal of the bracket from the tooth. The novel method and means for bonding of orthodontic brackets to teeth, or other bonding procedures, is simple and efficient in operation and economical and durable in construction.

BRIEF DESCRIPTION OF THE DRAWINGS

FIG. 1 is a side elevational view of an ultrasonic implement embodying the invention.

FIG. 2 is a side elevational view of an ultrasonic implement embodying the invention in combination with a tooth and illustrates one step in the bonding of an orthodontic bracket to a tooth.

FIG. 3 is a side elevational view of another ultrasonic implement embodying the invention and illustrates another step in the bonding of an orthodontic bracket to a tooth.

FIG. 4 is an enlarged side elevational view of a typical orthodontic bracket and illustrates one embodiment of a bonding operation embodying the invention.

FIGS. 5 through 9 are side elevational views of ultrasonic attachment devices embodying differing modifications of the invention with some portions shown in section for purposes of illustration.

FIG. 10 is an enlarged side elevational view of a typical orthodontic bracket illustrating a modification of the bracket embodying the invention.

FIG. 11 is an enlarged side elevational view of a sonic bonding element embodying the invention.

FIG. 12 is a side elevational view of a further sonic implement embodying the invention with an enlarged orthodontic bracket shown in broken lines.

DETAILED DESCRIPTION OF THE PREFERRED EMBODIMENTS

Figure 13:
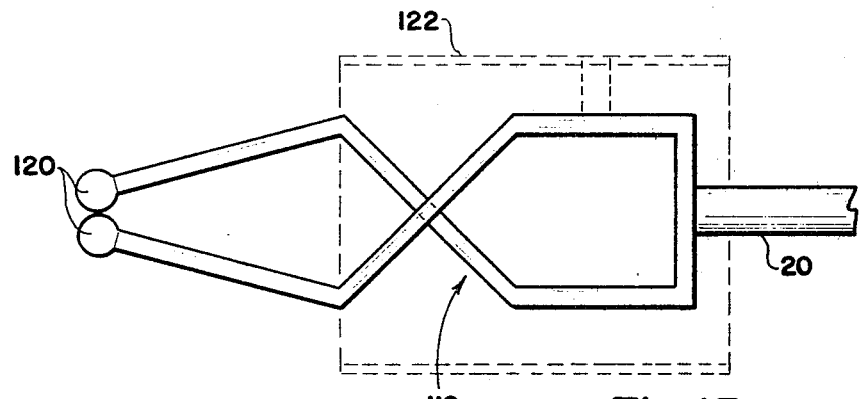
FIG. 13 is a side elevational view of a still further sonic implement embodying the invention, with portions shown in broken lines for purposes of illustration.

Referring to the drawings in detail, and particularly FIGS. 1 and 2, reference character 10 generally indicates an ultrasonic implement for facilitating a bonding operation between at least two articles or objects. Of course, it is to be noted that the present invention is not limited to ultrasonic energy in that any sonic energy found effective may be used, but for purposes of illustration, the devices and implements described herein will be referred to as ultrasonic instruments. In other words, the term ultrasonic energy generally denotes vibrations in excess of 20,000 HZ; however, sonic vibrational energy of substantially any desired frequency may be used in the practice of this invention.

The implement 10 comprises an ultrasonic generator 12 having a suitable control apparatus 14 operably connected therewith. The generator 12 is preferably of an electrical variety, but it is to be understood that any other suitable source of ultrasonic energy may be used, including electromechanical. In addition, the control apparatus 14 preferably includes the usual on/off switch, timer control, variable frequency and auto frequency control, variable pulse control, variable waveshape control, frequency sweep control, multiple frequency combination control, constant or variable amplitude and displacement controls, pressure sensing and hold time activation and deactivation, load sensing and activation and compensation and deactivation control, alarm features, with programmed sequence of events or combinations, none of which are shown in detail herein. Of course, conventional electronic circuits, controls, transducers and sensors may be located throughout the structure of the control apparatus 14 and other structures, as is well known.

The generator 12 is connected through a coaxial cable 16 to a suitable transducer 18. There are many different types and shapes of transducers which are suitable for use, with piezoelectric transducers having been found to be effective and efficient for the present purposes. Attached to and extending from the output side of the transducer 18 is a horn 20 which directs the ultrasonic energy to an elongated rod 22 which is connected to the horn 20 in any suitable manner (not shown). The rod 22 is preferably constructed from any sound transmissive material, such as steel, titanium, or glass. The rod 22 should allow for a limited range of deflection or bending in the operation of the device 10. An alternate configuration of the rod 22 may be comprised of a single or a plurality or bundle of metallic rods or flexible tuned transmission lines 24 extending from the horn 20 so as to provide a greater range of deflection. The major direction of vibration is along the longitudinal axis of the horn 20 as shown by the arrow A. Other modes of vibrations and waves can also be utilized, singularly or in combination.

As hereinbefore set forth, the ultrasonic generator 12 may be of any desired type, such as electrical, pneumatic, hydraulic or mechanical. The transducer means 18 may be of any type cooperable with the generator means 12 and may be piezoelectric, electrostrictive, magnetostrictive, or a suitable resonating structure. In addition, the transducer means 18 may be formed from poly crystalline material, such as PZT lead zirconate titanate, which can be formed in any desired shape and polarized to be the transducer.

In the bonding of the bracket 28 to the tooth 26, it may be that a particular application of complementary materials or chemicals may be advantageously applied to the rearward surface 34 of the bracket 28 as shown in FIG. 4. For example, a first primer layer 36 may be initially applied to the surface 34, with an adhesive layer 38 superimposed over the primer layer 36. A second primer layer 40 may be applied or superimposed over the adhesive layer 38, followed by a layer 42 of a suitable abrasive material, such as diamonds, or the like. Of course, the particles in each layer are of a micron or submicron size, and may be encapsulated if desired. Of course, it will be apparent that these layered or encapsulated materials may be preformed or prepackaged in a storage means and applied as a single unit. Alternatively, the particles may be intermingled in the layers rather than strictly layered by composition. The application of the sonic or ultrasonic frequency to the bracket 28 is transmitted to the layered particles on the surface 34 thereof for quickly and efficiently mixing of the various elements and bonding the bracket 28 to the surface of the tooth 26. In the event the particles in the layers are encapsulated, the sonic frequency provides sufficient pressure for breaking or rupturing the capsules to release the contents for mixing with the other components of the layers. The layered materials provide a sonic etching, cleaning and bonding process.

Of course, it will be further apparent that other combinations of layered materials may be applied to the surface 34 of the bracket 28 to achieve an efficient end result in the bonding process. In addition, it may be desirable to provide a plurality of minute fibers 35 or cutting particles as shown in FIG. 10, on the surface 34 of the bracket 28 in lieu of the chemicals or with encapsulations or layers as hereinbefore set forth, said fibers or particles preferably being of approximately thirty microns in length and arranged in a prismatic structure as will be hereinafter set forth. These fibers or cutting particles 35 actually drill into the tooth surface upon the application of sonic energy to the bracket 28. Alternatively, an intermediate fiber or cutting particle structure 37 (FIG. 11) having fibers or cutting particles 39 extending outwardly from one side, both sides, or around the entire outer periphery thereof may be independent of the bracket 28, and interposed between the bracket 28 and the tooth 26, if desired. These fibers 39 will drill into the surface of the tooth and/or the attaching structures for an efficient bonding therebetween.

As hereinbefore set forth and as is well known, the etching of the teeth usually produces etching patterns in the tooth enamel of a honeycomb structure or prismatic. Thus, it may be desirable to arrange the fibers 24 with the outer ends thereof in relatively off-sect relationship corresponding to the etching pattern of the tooth enamel. In this manner, the fibers 24 may produce a more efficient operation during a bonding operation, or the like. Of course, not only the fibers 24, but all cutting particles, abrasives, optical fibers, laser fibers, either sonic or electrical may be arranged in a honeycomb or prismatic pattern corresponding to the etching pattern on the tooth enamel, if desired.

It is important to note that the encapsulation or layered concept is of particular value in the field of dentistry, bone bonding and many other processes. A further concept is to provide time released layers or encapsulation that is released, mixed, and activated, depending on the molecular or structural resonance, heat, pressure, frequency and power applied, where each stage is momentarily activated in a particular program sequence. For example, in this instance, the initial layer applied to the surface 34 of the bracket 28 may be a primer layer, with an adhesive layer superimposed thereon and followed by a filler layer and a second primer layer. A neutralizer layer may be applied subsequent to the second primer layer, and the neutralizer layer may be followed by a suitable acid layer. When sonics are applied, the acid layer or barrier or encapsulation ruptures, etching the tooth, the neutralizer stage erupts reacting with the acid, and the other stages rupture, mix and then bond the bracket 28 to the tooth 26. Of course, these layers or encapsulation materials may be of substantially any suitable desired thicknesses, density, wave length, and various chemical compositions.

It has been found that the application of ultrasonics to the bracket 28 when one of the super glues is used as a bonding agent, no etching of the tooth is required, thus providing a rapid and strong bonding in literally seconds. Experimentation has also been made with the use of super glue in combination with fillers, such as paper, bone powder, enamel tooth powder, plastic, and/or abrasives, and excellent bonding results have been achieved. Of course, some of these additives may be used in and of themselves as the bonding agent.

Referring now to FIGS. 5 through 9, additional embodiments of the invention are shown all of which comprise threaded attachment elements which may be threadedly connected at the outer end of the horn 20 in lieu of the rod 22 or fibers 24. The attachment generally indicated at 44 in FIG. 5 comprises a rod 46 having a threaded portion 48 provided at one end thereof for connection with the outer end of the horn 20, and having a flexible screen means 50 provided at the outer end thereof. Preferably a plurality of minute abrasives, such as diamonds, or brushes, or combinations thereof are suitably secured to the outer surface of the screen means 50. This fibrous screen may be epoxy coated, if desired. In addition, it may be desirable to provide a back plate means 52 secured on the rod 46 and interposed between the screen means 50 and the threaded portion 48. When the plate means 52 is utilized, the outer edges of the screen means 50 may be suitably secured to the plate. It may also be preferable or desirable to provide conduits 54 extending into communication with a suitable vacuum source, or into communication with suitable fluids, as desired, and as set forth in my co-pending application Ser. No. 232,425.

Of course, the vacuum return conduit means may surround the attachments or implement, or comprise open conduits disposed in communication with the work area for removal of debris, or the like, as an operation or work is being performed with the use of the implement 10. It is also to be noted that the attachments shown herein may be utilized either with or without a vacuum return line, and with or without means for application of fluids, and if desired, freezing mediums may be utilized to provide a freezing spray at the work area.

A modified attachment 56 is shown in FIG. 6 which is generally similar to the attachment 44 and comprises a rod means 58 having a threaded portion 60 on one end thereof for connection with the horn 20, and a contact means 62 provided at the opposite end thereof. A plurality of mixed flexible materials, such as soft metals, elastomer, foam metals, and/or other abrasives and other structures or ultrasonically mixed compositions, may be adhered to the outer surface of the contact means 62. In addition, a coil means 64 may surround the outer periphery of the rod 58. The coil may contain a heating and/or cooling or freezing or super cooling coil medium to alter the hardness and sonic transmitting properties of the impression and the etching materials as well as the bonding materials and applied structures. The application of heat can cause deformation of the bonding material into a conformation corresponding to the surface or article upon which it is to act, and the freezing set the deformed material or hardens the material in the deformed configuration, thus permitting sonic frequency or energy to be transmitted between the articles being bonded or etched more efficiently.

FIG. 7 shows still another attachment 66 comprising a flexible cone means or apron 68 having the outer face thereof coated with Teflon (a trademark of E. I. DuPont De Nemours and Co.) or the like, and having a plurality of accessed control lines 70 providing communication between the interior and exterior thereof. The lines 70 may extend into communication with a source of acid, polishers, bleaches, vacuum, abrasives, gases, or the like and are provided with any suitable non-stick coating. It is preferable to provide a suitable two-way valve 71 in each of the lines 70 and disposed in the proximity of the cone 68 for controlling the flow of the fluid through the lines and into the interior of the cone means.

FIG. 8 illustrates a further attachment 72 comprising a rod means 74 having one end threaded at 76 for connection with the horn 20, and having a contact or head means 78 at the opposite end thereof, the head means 78 preferably being constructed from single or multiple layers of foil and pressurized by internal gas or fluids or optional external abrasive. Where no etching or cleaning of the surface to which an article is to be bonded is required, but only impressions or bondings are to be made, the fibers or abrasives as shown hereinbefore are not needed in any of the attachments described and illustrated herein.

It is usually necessary to remove the bracket 28 from the tooth 26 when the bracket is no longer of use. A sonic integument removal device 108 generally similar to that shown in my aforementioned co-pending application Ser. No. 194,869 and shown in FIG. 12 may be utilized not only for the bonding of the bracket 28 to the tooth 26, but also for removal of the bracket from the tooth, or bonding and/or removal of substantially any object to another object. The device 108 is a pincer-type implement having a pair of pivotal arm members 110 and 112, with one of the arms, as for example the arm 110, being the sonic transmission line or horn. The sonic arm 110 may be slightly elongated at the outer end thereof as shown at 114 for engagement with the exposed elements of the bracket 28. With the end 114 in engagement with the bracket 28, the application of sonic frequency along the arm 110 and to the bracket 28 through the end 114 causes a bonding or release of the bond between the bracket 28 and the tooth 26, as required. When the bracket is released from the bonded engagement with the tooth 26, the bracket may be removed from the tooth along with the implement 108.

Referring particularly to FIGS. 2 and 3, a method of bonding the bracket 28 to the tooth 26 is shown. The implement 10 may be utilized for cleaning of the tooth 26 in the general manner as set forth in my aforementioned co-pending application Ser. No. 232,425. In this instance, the fibers or bristles 24 may be utilized in lieu of the line 22, and the bristles are impressed with ultrasonic frequency in the usual manner. A very quick and slight engagement of the fibers 24 with the surface of the tooth 26 will provide a very efficient cleaning of the tooth surfaces. The usual etching acid may be applied to the surface of the tooth 26 in the well known manner, and the application of the sonic or ultrasonic power through the fibers 24 will atomize or dissipate the chemicals applied in addition to increasing the speed of the etching process. Thus, the tooth 26 may be quickly and efficiently initially cleaned, etched, and subsequently cleaned in preparation for receiving the orthodontic bracket 28 thereon.

It may be preferable to arrange the fibers 24 in a "prism" configuration to coincide or cooperate with the usual prism etching of the tooth. This creates a plurality of prism configurations on the planar area defined by the fiber tips.

Substantially any desired bonding agent may be applied to the reverse or rearward surface of the bracket 28 and/or the prepared surface of the tooth 26, or the bracket may be provided with the fibers 35, or the element 37 may be interposed between the bracket 28 and the tooth 26, with the bracket being positioned at the desired location against the surface of the tooth. When the bracket 28 has been so positioned, sonic energy may be transmitted to the bracket 28 by engaging the bracket with the outer end 114 of the implement 108. Of course, the bracket 28 may be initially picked up by the engagement of the end 114 therewith and the tool or implement 108 may be properly manipulated for positioning the bracket at the desired location against the surface of the tooth 26. The sonic energy applied to the bracket causes the bonding agent to quickly form a bond between the tooth and the bracket 28, said bond being of much greater strength than otherwise possible. As hereinbefore set forth, some of the super glues have been found to provide extremely great bonding between the tooth and the bracket.

Of course, the bracket may be released from the bonded engagement with the tooth by re-engaging the end 114 of the implement 108 therewith and applying sonic energy through the horn or arm 110 as hereinbefore set forth.

Figure 14:
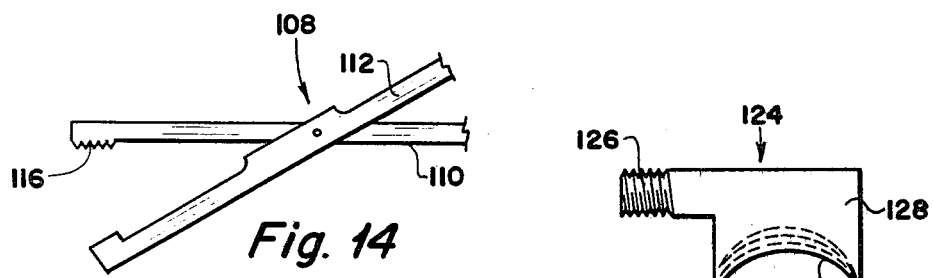
FIG. 14 is a side elevational view of yet another modified sonic implement embodying the invention.

A modification of the implement 108 is shown in FIG. 14 wherein the outer ends or engagement ends of one of the arms as for example the arm 110 may be provided with blade means 116, with or without abrasives or serrations or transmitting fibers, and the engagement end of the other arm 112 may be provided with an elastomer coating and is configured either with or without a groove inside the outer tip thereof.

Another sonic removal device or bonding grasping structure is shown at 118 in FIG. 13. This device is in the form of the well known normally closed tweezer or forceps type implement and is suitably connected with the sonic transmission line or horn 20. The outer ends of the gripper members of the implement 118 are optionally provided with a soft metallic or elastomer tip 120, and it may be desirable to provide a see through tube 122 constructed from Teflon, or the like, and which extends to a vacuum source or a gas pressure source.

Figure 15:
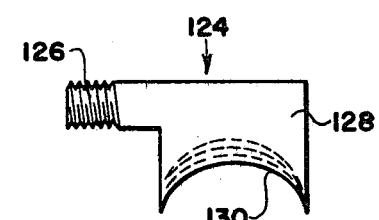
FIG. 15 is a view of a further modified sonic implement embodying the invention.

FIG. 15 shows an attachment 124 having a threaded portion 126 for connection with the outer end of the horn 20, and a head means 128 having an arcuate outer end 130 particularly configured for engagement with a socket member (not shown), such as used in a hip replacement system operation, or the like. The arcuate end 130 may be positioned against the outer periphery of the socket member and actuated in the manner as hereinbefore set forth for transmitting sonic frequencies or ultrasonic energy to the socket member for facilitating the healing and/or bonding of the hip socket member to the hip bone structure.

Figure 16:
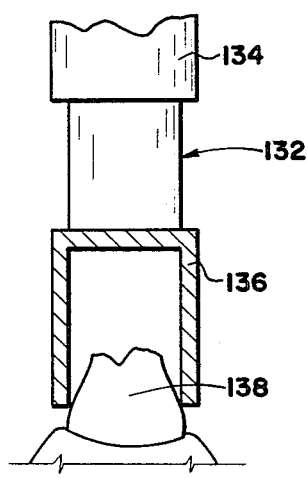
FIG. 16 is a view of a further modified sonic implement illustrated in combination with a broken tooth.

Another feature of the sonic method and means of the present invention as applied in the dental field is shown in FIG. 16. An attachment generally indicated at 132 may be secured to the outer end of the horn 20 or transmission line in any suitable manner and a socket member or open sleeve 136 may be provided on the outer end of the device 132 for telescoping over the outer end of a broken tooth 138. The sonic bonding methods as hereinbefore set forth may be applied to bond the enveloping sleeve or tube member 136 to the broken tooth 138 and the application of the sonic frequency to the tooth 138 through the bonded sleeve 136 gently loosens the tooth for ready extraction.

Figure 17:
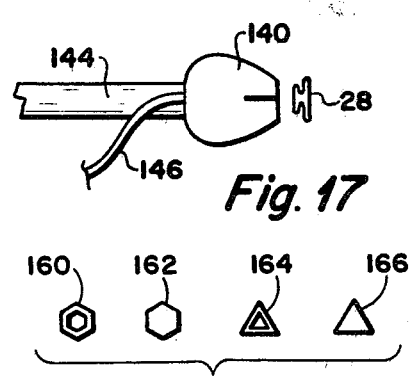
FIG. 17 is a side elevational view of still another sonic implement embodying the invention.

Another aspect of the invention is shown in FIG. 17 wherein a cup member 140 is open at one end thereof and may be provided with axially extending slits or a simple recessed area 142 which may grip or engage the outer periphery of a tooth or be arranged thereover in such a manner that the tooth may be disposed within the cup 140, if desired. A sonic line 144 is operably secured to the cup 140 in any well known manner as hereinbefore set forth, and it may be desirable to provide conduit means 146 to provide communication between the interior of the cup 140 and a vacuum source, or chemical or gas pressure source, as hereinbefore set forth. This device may not only be utilized for bonding of the bracket 28 and removal of the bracket 28 in a manner as hereinbefore set forth, but also may be utilized for tooth extraction and impressions. Suitable impression material may be placed within the cup 140 and the application of sonic frequency to the cup 140 through the line 144 in the well known manner will facilitate the setting up of the impression material for quickly providing a dental impression. It is important to note that substantially any bondable structure may have bonding agents between the sonic transmitting line and the structure to be bonded next to provide maximum sonic transmitting efficiency for the primary bonding function. Then the temporary bonding agent may be broken and removed.

It is to be noted that any auxiliary equipment such as coils, and the like, must be positioned at a node of the implements, as is well known, unless it is desirable to pass the sonic energy through the auxiliary equipment. RTV silicone insulation can be applied to any desired surface to block the passage of sound, electricity and heat. Of course, any of the forceps, tweezers, or the like, may be bent or formed as desired without effecting the aforementioned results. For most efficient sound transmission, metal, glass and hard materials are preferable for maximum efficiency. In addition, the cooling and freezing mediums can alter the efficiency of the elastomers and other materials.

Figure 18:
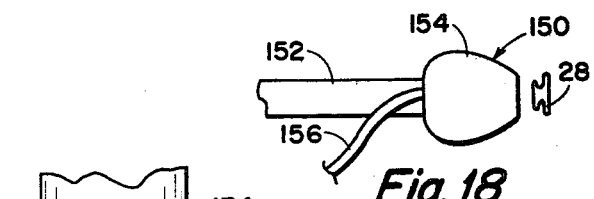
FIG. 18 is a side elevational view of a still further sonic implement embodying the invention.

FIG. 18 shows a one-handed type gripping and releasing means 150 for etching and bonding structures in the general manner as hereinbefore set forth. The device 150 may comprise the usual sonic line 152 connected with a hollow cup member 154 which may be partially filled with any of the previously mentioned bonding structures, or may be a slightly flexible metal or glass structure provided with slots (not shown). The interior of the cup 154 may be in communication with a vacuum source (not shown) or gripping means through a line or conduit 156, or the line 156 may be a chemical or a gas pressure release or input line. The bracket 28 may be inserted, or other matching size structures may be used if desired in lieu of the bracket, depending on the diameter of the cup opening and the matching or near matching shape or configuration of the tip and cavity design of the cup 154. This device may be used for both tooth extraction and impressions.

It is also important to note that any bondable structure may have bonding agents between the sonic transmitting line and the structure to be next bonded to have maximum sonic transmitting efficiency for the primary bonding function. Then, the temporary bonding agent may be broken and removed.

Figure 19:
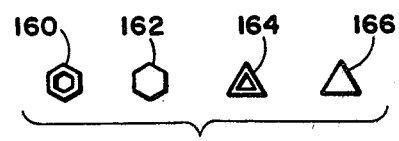
FIG. 19 shows enlarged end views of possible configurations for the bristles or fibers utilized in the invention.

As hereinbefore set forth honey comb or prism shaped abrasives, brushes, or fibers, whether sonic, electrical or laser may be of an advantage in the etching and/or bonding operation. As shown in FIG. 19, the fibers, bristles, abrasives, or the like may be of a substantially hexagonal or honey comb cross section configuration, either hollow as shown at 160 or solid as shown at 162 and with optional internal and/or external reflective coatings. Alternatively, the fibers, bristles, abrasives, or the like may be of a prismatic cross sectional configuration, either hollow as shown at 164 or solid as shown at 166. Of course, either configuration may also be of a fibrous construction as hereinbefore set forth.

From the foregoing it will be apparent that the present invention provides a novel method and means for bonding an orthodonic bracket to a tooth, or the like. The cleaning and etching of the tooth, as required, may be readily accomplished by utilizing the sonic brush means of the invention whereby the overall bonding operations is not only accomplished rapidly, but the bond between the tooth and the bracket is extremely strong. In addition the same sonic principle may be utilized for release of the bonded bracket when the use of the bracket is no longer required.

Whereas the present invention has been described in relation to the drawings attached hereto, it should be understood that other and further modifications, apart from those shown or suggested herein may be made within the spirit and scope of this invention.

What is claimed is:

1. Sonic apparatus for bonding one article to another and comprising sonic transmission line means in operable connection with one of the articles for transmitting sonic energy thereto, and bonding agent means interposed between the articles for response to the sonic energy to bond the articles together upon engagement therebetween, one of said articles being a tooth and the other article being an orthodontic bracket, and wherein the sonic transmission line is connected to pincer means, said pincer means being provided with article engaging means for holding the orthodontic bracket in engagement with the tooth during the bonding operation.

2. Sonic apparatus as set forth in claim 1 and including vacuum source conduit means disposed in the proximity of the engaged articles and open to the area therearound.

3. Sonic apparatus as set forth in claim 1 and including gas conveying conduit means disposed in the proximity of the engaged articles and in communication therewith.

4. Sonic apparatus as set forth in claim 1 wherein bonding fibers are provided for facilitating the bonding operation.

* * * * *